US006455627B1

(12) United States Patent
De Keyzer et al.

(10) Patent No.: US 6,455,627 B1
(45) Date of Patent: Sep. 24, 2002

(54) HOT MELT PRESSURE SENSITIVE POSITIONS ADHESIVE (II)

(75) Inventors: Noël Raymond Maurice De Keyzer, Ottignies (BE); Carolyn Ann Stoner, Houston, TX (US)

(73) Assignee: Kraton Polymers US LLC, Houston, TX (US)

(*) Notice: Subject to any disclaimer, the term of this patent is extended or adjusted under 35 U.S.C. 154(b) by 0 days.

(21) Appl. No.: 09/599,755

(22) Filed: Jun. 22, 2000

Related U.S. Application Data

(60) Provisional application No. 60/141,144, filed on Jun. 25, 1999.

(51) Int. Cl.[7] .................. C08K 5/01; C08L 93/04; C08L 53/00
(52) U.S. Cl. ............... 524/505; 524/271; 524/274; 524/474; 524/485; 524/486; 524/490; 524/484; 524/491; 525/98; 525/99
(58) Field of Search ................. 524/505, 474, 524/485, 486, 490, 491, 484, 271, 274; 525/98, 99

(56) References Cited

U.S. PATENT DOCUMENTS

| | | | | |
|---|---|---|---|---|
| 4,136,699 A | | 1/1979 | Collins et al. ......... 128/290 R |
| 4,526,577 A | | 7/1985 | Schmidt, Jr. et al. ....... 604/366 |
| 4,857,594 A | * | 8/1989 | Lakshmanan et al. ........ 525/98 |
| 5,163,976 A | * | 11/1992 | Ravipati et al. ............. 51/295 |
| 5,331,038 A | * | 7/1994 | Dillman .................... 524/505 |
| 5,332,613 A | * | 7/1994 | Taylor et al. .............. 428/152 |
| 5,356,963 A | * | 10/1994 | Kauffman et al. ............ 524/33 |
| 5,360,854 A | * | 11/1994 | Bozich, Jr. .................. 524/505 |
| 5,459,193 A | | 10/1995 | Anderson et al. ........... 524/505 |
| 5,486,387 A | * | 1/1996 | Mueller .................... 428/34.7 |
| 5,618,883 A | * | 4/1997 | Plamthottam et al. ........ 525/98 |
| 5,627,235 A | * | 5/1997 | Gimes .......................... 525/98 |
| 5,703,162 A | * | 12/1997 | Anderson .................. 525/89 |
| 5,741,840 A | * | 4/1998 | Lindquist et al. ........... 524/271 |
| 5,777,043 A | | 7/1998 | Shafer et al. ............... 525/339 |

FOREIGN PATENT DOCUMENTS

| | | | | |
|---|---|---|---|---|
| AU | 90/631250 | * | 4/1991 | .......... C09J/123/16 |
| DE | 3705992 | * | 8/1987 | ............. C08L/9/06 |
| EP | 0298319 A1 | * | 1/1989 | |
| EP | 0368102 A2 | * | 5/1990 | |
| EP | 0428017 A2 | | 10/1990 | .......... C09J/193/00 |
| EP | 0397100 | * | 11/1990 | .......... B32B/27/00 |
| EP | 0431391 | * | 6/1991 | .............. C09J/9/00 |
| EP | 0525251 A1 | | 12/1991 | .......... C09J/153/00 |
| EP | 0289609 B1 | * | 2/1992 | |
| EP | 0802251 A1 | | 4/1996 | .......... C09J/153/02 |
| EP | 0798358 A1 | * | 10/1997 | |
| JP | 57055980 | | 4/1982 | ............. C09K/3/10 |
| JP | 61152759 | | 7/1986 | .......... B65D/90/04 |
| JP | 01256583 | | 10/1989 | .............. C09J/7/02 |
| JP | 03162730 | | 7/1991 | .............. C09J/7/02 |
| JP | 03258844 | | 11/1991 | .......... B32B/27/30 |
| JP | 05002325 | | 1/1993 | .............. C09J/7/02 |
| JP | 05008954 | | 2/1993 | .......... C09J/153/02 |
| JP | 06228527 | | 8/1994 | .......... C09J/201/00 |
| JP | 06228529 | * | 8/1994 | .......... C09J/201/00 |
| JP | 08073822 | | 9/1994 | .............. C09J/7/02 |
| JP | 07304911 | * | 11/1995 | .......... C08L/23/16 |
| JP | 2791396 | | 8/1998 | .......... C09J/121/00 |
| JP | 10298514 | * | 11/1998 | .............. C09J/7/02 |
| WO | WO 95/30721 | | 11/1995 | .......... C09J/153/02 |
| WO | 98/00471 | * | 1/1998 | |

OTHER PUBLICATIONS

Cigana et al., *Macromolecules,* 30(14) pp. 4163–4169, 1997 (Abstract).*
Nishikawa et al., *Polym. Prepr. (ACS, Div. Polym. Chem.),* 37(2), pp. 702–703, 1996 (Abstract).*

\* cited by examiner

*Primary Examiner*—Margaret Medley

(57) ABSTRACT

The present invention is a hot melt pressure sensitive positioning adhesive for use with an absorbent article. The adhesive comprises:

(a) from 6 to less than 15 percent by weight, of the total of (a), (b) and (c) of a blend of
  (i) from 40 to 95% by weight of a hydrogenated styrene-(butadiene and/or isoprene)-styrene block copolymer; and
  (ii) from 5 to 60% by weight of a blend of a hydrogenated styrene-isoprene-styrene-isoprene block copolymer; and
  (iii) from 0 to 40% by weight of an amorphous ethylene/propylene copolymer having a number average molecular weight of 9,000 to 30,000; and (b) from 50 to 80 percent by weight, of the total of (a), (b) and (c), of a tackifying resin which has an aromaticity such that the MMAP cloud point is at least 45° C.; and (c) from 5 to 35 percent by weight, of the total of (a), (b) and (c), of a plasticizer.

10 Claims, No Drawings

HOT MELT PRESSURE SENSITIVE POSITIONS ADHESIVE (II)

This application claims the benefit of Provisional Application No. 60/141,144, filed Jun. 25, 1999.

FIELD OF THE INVENTION

This invention relates to hot melt pressure sensitive positioning adhesives for use with absorbent articles which are based on blends of hydrogenated block copolymers of styrene and butadiene or isoprene and exhibit improved viscosity and viscosity/temperature profile.

BACKGROUND OF THE INVENTION

Positioning adhesives are used on disposable articles (absorbent articles) such as sanitary napkins, incontinent pads, bed pads, feminine pads, panty shields, diaper inserts, etc. where an adhesive layer is used to attach the article to a woven fabric substrate such as a supporting undergarment or bed sheet. The positioning adhesive is commonly applied to a release liner and transfer coated to the garment facing surface of the disposable article. The positioning adhesive must be capable of attaching to the undergarment to hold the article in place without transferring to or otherwise being deposited on the undergarment. Furthermore, the adhesive must not discolor, damage, or disturb the fibers of the garment.

The positioning adhesive must be a pressure sensitive adhesive that has an application viscosity that permits it to readily flow onto and partially penetrate the particular surface to which it is applied. It must have good bond strength and high tack for initial placement of the article on the undergarment but also must have the ability to avoid loss of adhesion over time due to temperature conditions. Finally, these articles are sometimes used for long periods of times at body temperature and they can have the drawback that the hot melt adhesive gradually softens and penetrates into the undergarment to which the article is adhering. In this case, the adhesive force greatly increases and the cohesive force is reduced. This causes the adhesive layer to suffer cohesion breakdown when the article is removed and some adhesive remains on the undergarment. Prevention of this deposit of adhesive on the undergarment is accordingly a necessary prerequisite for a successful positionable hot melt adhesive composition.

Block copolymers of styrene and dienes such as butadiene or isoprene have been used for a number of years in positionable hot melt adhesive formulations. More recently, the material of choice for such adhesives in feminine care applications has been hydrogenated block copolymers of styrene and butadiene such as KRATON® G1650 SEBS (hydrogenated styrene-butadiene-styrene) block copolymer. Formulations based on these SEBS block copolymers have been found to have excellent adhesion to fabrics like cotton and nylon and have the advantage that they leave no residue after peeling. The application viscosity of formulations using these polymers is acceptable but it would be advantageous to have a positionable adhesive formulation which has a lower viscosity in order to lower the application temperature. This reduces the risk of degradation, char forming, and filter plugging. This also results in energy and cost savings, decreases maintenance costs, and reduces the amount of odor due to the volatiles coming from the adhesive. The present invention provides such an improved positionable hot melt adhesive formulation.

SUMMARY OF THE INVENTION

The present invention is a hot melt pressure sensitive positioning adhesive for use with an absorbent article. The adhesive comprises:

(a) from 6 to less than 15 percent by weight, of the total of (a), (b) and (c) of a blend of
  (i) from 40 to 95% by weight of a hydrogenated styrene-(butadiene and/or isoprene)-styrene block copolymer; and
  (ii) from 5 to 60% by weight of a blend of a hydrogenated styrene-isoprene-styrene-isoprene block copolymer; and
  (iii) from 0 to 40% by weight of an amorphous ethylene/propylene copolymer having a number average molecular weight of 9,000 to 30,000; and
(b) from 50 to 80 percent by weight, of the total of (a), (b) and (c), of a tackifying resin which has an aromaticity such that the MMAP cloud point is at least 45° C.; and
(c) from 5 to 35 percent by weight, of the total of (a), (b) and (c), of a plasticizer.

DETAILED DESCRIPTION OF THE INVENTION

One of the primary components of the positioning adhesive composition of the present invention is the above-described hydrogenated block copolymer that has two polystyrene endblocks and a saturated or hydrogenated polybutadiene and/or polyisoprene midblock. This conventional hydrogenated base block copolymer provides the primary load bearing capability of the adhesive composition. It is important that the polymer be hydrogenated so that the structural integrity of the polymer is preserved even if outside forces that cause degradation are encountered. The block copolymer may be hydrogenated as generally described in the prior art, preferably so as to reduce at least 90 percent of any olefinic double bonds in the polymer chains. Suitably at least 50 percent, preferably at least 70 percent, and more preferably at least 90 percent, most preferably at least 95 percent of the original olefinic unsaturation is hydrogenated.

Anionic polymerization of conjugated diene hydrocarbons with lithium initiators is well known as described in U.S. Pat. Nos. 4,039,593 and Re. 27,145 which descriptions are incorporated herein by reference. Polymerization commences with a monolithium, dilithium, or polylithium initiator which builds a living polymer backbone at each lithium site. Typical living polymer structures containing polymerized conjugated diene hydrocarbons are:

X—B—Li

X—A—B—Li

X—A—B—A—Li

Li—B—Y—B—Li

Li—A—B—Y—B—A—Li wherein B represents polymerized units of one or more conjugated diene hydrocarbons such as butadiene or isoprene, A represents polymerized units of one or more vinyl aromatic compounds such as styrene, X is the residue of a monolithium initiator such as sec-butyllithium, and Y is the residue of a dilithium initiator such as the diadduct of sec-butyllithium and m-diisopropenylbenzene. Some structures, including those pertaining to polylithium initiators or random units of styrene and a conjugated diene, generally have limited practical utility although known in the art.

In general, the polymers useful in this invention may be prepared by contacting the monomer or monomers with an organoalkali metal compound in a suitable solvent at a temperature within the range from −150° C. to 300° C., preferably at a temperature within the range from 0° C. to 100° C. Particularly effective polymerization initiators are organolithium compounds having the general formula:

$$RLi$$

wherein R is an aliphatic, cycloaliphatic, alkyl-substituted cycloaliphatic, aromatic or alkyl-substituted aromatic hydrocarbon radical having from 1 to 20 carbon atoms.

Suitable solvents include those useful in the solution polymerization of the polymer and include aliphatic, cycloaliphatic, alkyl-substituted cycloaliphatic, aromatic and alkyl-substituted aromatic hydrocarbons, ethers and mixtures thereof. Suitable solvents, then, include aliphatic hydrocarbons such as butane, pentane, hexane, heptane and the like, cycloaliphatic hydrocarbons such as cyclohexane, cycloheptane and the like, alkyl-substituted cycloaliphatic hydrocarbons such as methylcyclohexane, methylcycloheptane and the like, aromatic hydrocarbons such as benzene and the alkyl-substituted aromatic hydrocarbons such as toluene, xylene and the like and ethers such as tetrahydrofuran, diethylether, di-n-butyl ether and the like.

The hydrogenation of these polymers may be carried out by a variety of well established processes including hydrogenation in the presence of such catalysts as Raney Nickel, noble metals such as platinum, palladium and the like and soluble transition metal catalysts. Suitable hydrogenation processes which can be used are ones wherein the diene-containing polymer or copolymer is dissolved in an inert hydrocarbon diluent such as cyclohexane and hydrogenated by reaction with hydrogen in the presence of a soluble hydrogenation catalyst. Such processes are disclosed in U.S. Pat. Nos. 3,113,986, 4,226,952 and Reissue 27,145, the disclosures of which are herein incorporated by reference. The polymers are hydrogenated in such a manner as to produce hydrogenated polymers having a residual unsaturation content in polydiene blocks of less than about 1 percent, and preferably as close to 0 percent as possible, of their original unsaturation content prior to hydrogenation. A titanium catalyst such as disclosed in U.S. Pat. No. 5,039,755, which is herein incorporated by reference, may also be used in the hydrogenation process.

The molecular weights of linear polymers or unassembled linear segments of polymers such as mono-, di-, triblock, etc., or the arms of star polymers before coupling are conveniently measured by Gel Permeation Chromatography (GPC), where the GPC system has been appropriately calibrated. For anionically polymerized linear polymers, the polymer is essentially monodisperse (weight average molecular weight/number average molecular weight ratio approaches unity), and it is both convenient and adequately descriptive to report the "peak" molecular weight of the narrow molecular weight distribution observed. Usually, the peak value is between the number and the weight average. The peak molecular weight is the molecular weight of the main species shown on the chromatograph. For polydisperse polymers the weight average molecular weight should be calculated from the chromatograph and used. The materials used in the columns of the GPC are styrene-divinyl benzene gels or silica gels. The solvent is tetrahydrofuran and the detector is a refractive index detector.

As discussed above, the adhesive of the present invention contains from 6 to less than 15 percent by weight of a hydrogenated block copolymer of styrene and (butadiene or isoprene) and styrene (styrene-ethylene/butylene styrene—SEBS; or styrene-ethylene/propylene styrene—SEPS) in blend with a hydrogenated styrene-isoprene-styrene-isoprene block copolymer (styrene-ethylene/propylene—styrene-ethylene/propylene—SEPSEP) and, optionally, an amorphous ethylene/propylene copolymer. Preferably, 8 percent is necessary to get the best pressure sensitive adhesive properties and for the adhesive to be sufficiently cohesive. It is preferred that the maximum amount of the polymer be less than 15 percent by weight in order to keep the viscosity of the adhesive sufficiently low for the positioning adhesive application. More polymer than 15 percent can be used and good adhesion properties will be obtained but the viscosity will be unnecessarily increased.

The base triblock copolymer must have a sufficient molecular weight and polystyrene content to be useful for pressure sensitive adhesives. It will comprise from 40 to 95% by weight of the total polymer in the adhesive. Generally, the number average molecular weight should be from 65,000 to 300,000. If the molecular weight is less than 65,000 then the polymer loses its pressure sensitive adhesive properties. If the molecular weight is more than 300,000, then the polymer is not useful for adhesive applications. The polystyrene content should range from 10 to 40 percent by weight because this confers the right balance of cohesion and processability to the polymer.

The four block SEPSEP copolymer should have a number average molecular weight of 65,000 to 130,000, a polystyrene content of 13 to 30% by weight, and a polystyrene block molecular weight of 6,000 to 15,000. It will comprise from 5 to 60% by weight of the total polymer in the adhesive.

Amorphous polyalpha-olefins are low molecular weight, saturated homopolymers, like atactic homopropylene (APP) or copoylmers of ethylene/propylene (APE) like the Eastoflex grades E-1003, E-1060 or E-1200, or propylene/hexene copolymers (APH) like D-127 and the like from Eastman or terpolymers such as ethylene/propylene/butene like Vestoplast grades from Creanova (formerly Huels). Amorphous polyalpha-olefins are well known to be incompatible with styrene-ethylene/butylene-styrene block copolymers. However, it has been discovered that amorphous ethylene/propylene copolymers (APE) have acceptable compatibility hydrogenated styrene-isoprene block copolymers such as styrene-ethylene/propylene-styrene and styrene-ethylene/propylene-styrene-ethylene/propylene block copolymers.

Viscoelastic studies by dynamic mechanical analysis (Universal VI .10B TA instrument) show that blends of SEPS/APE(65/35%) show only one peak tan delta value with a significant shift from the peak tan delta value of the mid-block. Indeed, the peak tan delta of G-1730 is at −41° C., the peak tan delta of APE E-1060 is at −14° C., and the peak tan delta of the 65/35% by weight blend is at −34° C. Theoretical calculations of the peak tan delta value with the Fox equation, which assumes complete compatibility, give a value of the peak tan delta of the blend of −32° C. This value is very close to the measured one (−34° C.). This indicates a fair compatibility between SEPS and APE.

In comparison, a blend G-1657 (SEBS)/E-1060 (65/35%) gives the following values: the peak tan delta of G-1657 is −41° C., the peak tan delta of P-1023 is +3° C., and the peak tan delta value of the blend is −37° C. Theoretical peak tan delta value as calculated by the Fox equation gives a value of −29° C. This clearly indicates the poor compatibility of SEBS and APP.

I have discovered that the improved compatibility between SEPS and APE can be used to achieve some improvements in adhesive properties and particularly a higher peel on fabrics like cotton and nylon.

The APE of this invention disclosure have a weight average molecular weight of about 9,000 to about 30,000 and is determined on a Water 150C GPC that was calibrated with low-Mw polyethylene standard and a hot-melt viscosity between 200 and 25,000 cPs at @ 190° C. Further, these copolymers have a Ring and Ball softening point between 110° C. and 140° C. They are used in an amount of 0 to 40% by weight of the total polymer. If APE is used, the preferred range is 5 to 40% by weight. Such products are best described for example in the Eastman publications WA-4D and WA-67 and in *Advances in Pressure Sensitive Adhesive Technology*-2, edited by Don Satas in 1995.

It is known that one method to characterize tackifying resin compatibility is by determination of cloud points in suitable solvent systems. From the cloud point values obtained, the resin may be characterized as being aliphatic, aromatic, or a combination of both, polar or nonpolar, and having a high or low molecular weight. Hydrocarbon resins display wide variation in cloud point values and thus the cloud point concept is a useful method to characterize hydrocarbon resins.

MMAP cloud point is a well known measure of aromatic solubility and determines the aliphatic/aromatic character of the resin. The lower the MMAP cloud point, which is expressed in degrees centigrade, the more aromatic is the resin. A 1:2 mixture of methylcyclohexane and aniline is used as the solvent system in the MMAP cloud point determination. A standard weight of resin is dissolved in the solvent at high temperature and allowed to cool with mixing. The temperature at which the resin begins to separate out as an extra phase is determined to be the MMAP cloud point. This may be seen in the mixture as a cloudiness in the previously clear solution.

Suitable tackifiers may be selected from the group consisting of compatible $C_5$ hydrocarbon resins, hydrogenated $C_5$ hydrocarbon resins, styrenated $C_5$ resins, $C_5/C_9$ resins, styrenated terpene resins, fully hydrogenated or partially hydrogenated $C_9$ hydrocarbon resins, rosins esters, rosins derivatives and mixtures thereof. Of course, the tackifying resin must have an MMAP cloud point that is at least 45° C. in order for the polymer/resin blend to be compatible. Commercially available hydrocarbon tackifying resins for the present invention include PICCOTAC® 95 (MMAP=95° C.) as aliphatic resin, REGALREZ® series, like REGALREZ® 1085 (85° C.) or REGALREZ® 6108 (54° C.) and REGALITE® series, like REGALITE® V-1100 (48° C.) or REGALITE® S-260 (59° C.). REGALREZ® 3102 resin (MMAP=24° C.) does not work with these polymers because a phase stable blend cannot be achieved.

Suitable plasticizers like plasticizer oils include low aromatic content ($\leq 30\%$ wt, preferably $\leq 10\%$ wt) hydrocarbon oils that are paraffinic or naphthenic in character. Those products are commercially available from Shell Oil Company, like SHELLFLEX®, CATENEX®, ONDINA® oils, KAYDOL® oil from Witco, or TUFFLO® oils from Arco. Other plasticizers include compatible liquid tackifying resins like REGALREZ® R-1018. Other ingredients might also be added, like olefin oligomers, low molecular weight polymers like polybutene or liquid isoprene, low molecular weight copolymers, like liquid styrene/isoprene copolymers or hydrogenated styrene/isoprene copolymers, and copolymers like attactic polypropylene, vegetable oils and their derivatives, paraffin and microcrystalline waxes.

It is known in the art that various other components can be added to modify the tack, the odor, the color of the adhesives. Antioxidants and other stabilizing ingredients can also be added to protect the adhesive from degradation induced by heat, light and processing or during its shelf life, like during storage. Several types of antioxidants can be used, either primary antioxidants like hindered phenols or secondary antioxidants like phosphite derivatives or blends thereof. Examples of commercially available antioxidants are IRGANOX® 565 from Ciba-Geigy (2.4-bis-(n-octylthio)-6-(4-hydroxy-3,5-di-tertiary-butyl anilino)-1,3,5-triazine), IRGANOX® 1010 from Ciba-Geigy (tetrakis-ethylene-(3,5-di-tertiary-butyl-4-hydroxy-hydrocinnamate) methane) and POLYGUARD® HR from Uniroyal (tris-(2, 4-di-tertiary-butyl-phenyl)phosphite).

The adhesive composition of the present invention should have a viscosity of 100 to 10,000 cPs at 177° C., preferably from 600 to 6,000 cPs at 177° C. The adhesive must exhibit no transfer after being peeled away from a fabric. The adhesive composition is used in articles such as disposable diapers, sanitary napkins, bed pads, incontinent pads, surgical drapes, plasters, bandages, and the like.

EXAMPLES

All molecular weights are number average. KRATON G-1650 is a hydrogenated styrene-butadiene-styrene block copolymer having a molecular weight of 109,000, a polystyrene content of 30 percent by weight, and polystyrene block molecular weight of 10,000. KRATON G-1730 is a hydrogenated styrene-isoprene-styrene-isoprene block copolymer having a weight average molecular weight of 103,000, a polystyrene content of 21.5 percent by weight, and polystyrene block molecular weight of 6700. E-1060 is an amorphous ethylene/propylene copolymer (APE) having a Ring and Ball Softening Point of 135° C., a hot-melt viscosity of 6,000 cPs at 190° C., and a weight average molecular weight of 23,300.

Example 1

All the ingredients were compounded in a Z-blade mixer. Then the samples were put in beaker in an oven at 180° C. Once molten, the adhesive was poured onto a Mylar sheet and cast to obtain a thickness of 2 mils (50 microns). Prior to testing, the samples were conditioned at 23° C.—50%RH (relative humidity) for 24 hours.

Standard peel, tack and cohesion tests were carried out on these formulations. To assess the right functionality of the adhesive, specific adhesion tests on fabrics were performed, namely to evaluate the adhesion of the positioning adhesive onto the undergarment. Cotton and nylon fabrics are the two reference materials used in these tests.

The following peel adhesion tests on fabric were carried out:

Peel adhesion initial: for cotton, the initial peel is preferred to be in the range of 200–500 g/lineal inch.

Peel adhesion retention or aging test: the samples (fabric/adhesive/Mylar) are put in an oven at 40° C./8 hours under a load of 160 g/sq. in. Peel adhesion is determined after 1 hour conditioning at 23° C.—50R.H. Occurrence of adhesive transfer is also reported as none or transfer.

Adhesive transfer: the samples (fabric/adhesive/Mylar) are put in oven at 40° C./24 hours under a load of 800 g/sq. in. Peel adhesion is determined after 1 hour conditioning at 23° C.—50%R.H. Occurrence of adhesive transfer is also reported as none or transfer.

The SAFT (shear adhesion failure temperature) was measured by 1"×1" Mylar to Mylar lap joint with a 1 kg weight. SAFT measures the temperature at which the lap shear assembly fails under load. Rolling Ball Tack (RBT) is the distance a steel ball rolls on the adhesive film with a standard initial velocity (Pressure Sensitive Tape Council Test No. 6). Small numbers indicate aggressive tack. Holding Power (HP) is the time required to pull a standard area (½ in.×½ in.) of tape from a standard test surface (steel, Kraft paper) under a standard load (1 kg), in shear at 2° (Pressure Sensitive Tape Council Method No. 7). Long times indicate high adhesive strength. 180° peel was determined by Pressure Sensitive Tape Council Method No. 1. Large numbers indicate high strength when peeling a test tape from a steel substrate. Polyken probe tack (PPT) was determined by ASTM D-2979. Loop tack (LT) was determined using PSTC-5 loop tack method. High numbers for PPT and LT indicate aggressive tack. T-peel is measured by ASTM D-1876.

Table 1 below shows the results for the polymers alone and blended together. PICCOTAC® 95 is a trademark for an aliphatic hydrocarbon tackifying resin which is manufactured by Hercules. TUFFLO® 6056 oil is a plasticizing oil which is manufactured by ARCO.

Formulation F-2 based on G-1730 has adhesion initial properties close to G-1650 but with a much lower hot-melt viscosity. However, it exhibits transfer and is thus unacceptable. Formulation F-3, based on G-1730 and APE, has higher adhesion on fabrics than the G-1650 reference but unfortunately exhibits also transfer. Formulation F-4, a blend of G-1730, G-1650, and APE, shows a low hot-melt viscosity coupled with excellent adhesion on fabric without adhesive transfer. Formulation F-5, which is also a blend of G-1730, G-1650, and APE with a higher percentage of G-1730 than F-4 shows adhesive transfer. This indicates that the polymers can be blended to achieve a successful formulation but only in a limited ratio. Too much G-1730 causes transfer. A very important advantage of adding G-1730, i.e., to reduce the viscosity, is also proven here.

TABLE 1

| Formulation | F-1 | F-2 | F-3 | F-4 | F-5 |
|---|---|---|---|---|---|
| G1650 | 100 | | | 56 | 37.5 |
| G-1730 | | 100 | 75 | 19 | 37.5 |
| E1060 | | | 25 | 25 | 25 |
| Piccotac 95 V-1100 | 349 | 349 | 349 | 349 | 349 |
| Tufflo 6056 | 183 | 183 | 183 | 183 | 183 |
| Irganox 1010 | 3 | 3 | 3 | 3 | 3 |
| RC % | 15.70% | 15.70% | 15.70% | 15.7 | 15.7 |
| Kraton % | 15.70% | 15.70% | 11.80% | 8.8% G-1650 2.9% G-1730 | 5.9% G-1650 5.9% G-1730 |
| Hot Melt Visc. cPs | 1,830 | 660 | 439 | 634 | 490 |
| 180 Peel (steel) pli | 4.7 | 6.7 | 7 | 4.8 | 4.3 |
| 180 Peel Failure | Ghosting | Cohesive | Cohesive | Ghosting | Cohesive |
| HP Steel, 1 kg (min) | 39 A/G | 47 cohesive | 64 | 10 PC | 1 |
| SAFT Mylar 0.5 kg | 67 | 56 | 50 | 41 | 43 |
| Loop tack oz/in | 42* | | 87 | 122 | 136 |
| Adhesion initial | | | | | |
| T-Peel (cotton) pli | 0.5 | 0.6 | 1 | 0.6 | 0.8 |
| T-Peel (cotton) g | 225 | 270 | 445 | 270 | 360 |
| T-Peel (nylon) pli | 0.8 | 1.2 | 2 | 1 | 1.3 |
| T-Peel (nylon) g | 360 | 540 | 900 | 445 | 590 |
| Retention | | | | | |
| T-Peel (cotton) pli | 0.34 | | | 0.7 | 0.9 |
| T-peel (cotton) g | 150 | | | | |
| T-Peel (nylon) pli | 0.7 | | | 1.1 | 1.4 |
| T-peel (nylon (g) | 310 | | | | |
| Transfer | | | | | |
| T-Peel (cotton) pli | 0.81 | 2.52 ST | 2.89 MT | 0.9 | 2.8 T |
| T-peel (cotton) g | 360 | 1150 ST | 1300 MT | 400 | 1250 T |
| T-Peel (nylon) pli | 1.05 | 2.8 MT | 24.5 ST | 1.1 | 2.7 T |
| T-peel (nylon (g) | 470 | 1250 MT | 1108 ST | 500 | 1220 T |

T indicates transfer to the fabric
MT indicates a medium transfer
ST indicates a slight transfer Example 2

Table 2 shows the hot-melt viscosity in function of the temperature. The hot-melt viscosity is measured with a Bookfield Thermocell DVll-RV following ASTM D-3236-73. The formulation containing the blend G-1650, G-1730, and APE has a much lower hot-melt viscosity than the reference formulation based solely on G-1650. Formulation G-1650/G-1730/APE can be coated at much lower temperature than the G-1650 formulation.

TABLE 2

| Temperature ° F. | G-1650/G-1730/E-1060 59/19/25 CPs | G-1650 15.70% cPs |
|---|---|---|
| 275 | 6,750 | 73,300 |
| 300 | 2,435 | 16,240 |
| 325 | 1,418 | 4,570 |
| 350 | 634 | 1,800 |

Example 3

In this example, blends of various tackifying resins with varying MMAP values were tested with G-1650 for phase stability. The results are shown in Table 3 below.

TABLE 3

Compatibility SBC/resin blends in function of the aromaticity of the resin as defined by the MMAP cloud point

|  | R-3102 | V-1100 | S-260 | R-1085 | PICCOTAC 95 |
|---|---|---|---|---|---|
| MMAP° C. | 24 | 48 | 59 | 85 | 95 |
| G-1650 | I | C | C | C | C |

I = INCOMPATIBLE
C = COMPATIBLE

Example 4

The conditions for samples preparation and testing are given in example 1. In this example, two other polymers were evaluated in blends with G-1730 and APE. RP-6917 is a styrene-ethylene/butadiene-styrene block copolymer with 33% polystyrene content, a weight average molecular weight of about 280 000, and a 1,2 hydrogenated butadiene content of about 70%. RP-6918 is a styrene-ethylene/propylene-styrene block copolymer with 35% polystyrene content and a weight average molecular weight of about 270 000.

As seen in Table 4, formulation F-7 shows that when RP-6917 is compounded with G-1730 and APE, the hot-melt viscosity is decreased considerably compared to the formulation F-6 without G-1730. Moreover, formulation F-7 has higher adhesion on cotton and nylon, much higher than the reference formulation F-1 of example 1 based on G-1650. This effect is due to the synergy of G-1730 and APE.

RP-6918, compounded with G-1730 and APE in formulation F-9, shows higher adhesion on nylon and cotton than the reference formulation F-1 in example 1. When compounded with G-1730, the hot-melt viscosity is decreased considerably compared to formulation F-8 without G-1730.

TABLE 4

|  | F-6 | F-7 | F-8 | F-9 | F-10 |
|---|---|---|---|---|---|
| RP-6917 | 100 | 40 |  |  |  |
| RP-6918 |  |  | 100 | 75 | 37.5 |
| G-1730 |  | 35 |  |  | 37.5 |
| E-1060 |  | 25 |  | 25 | 25 |
| V-1100 | 349 | 349 | 464 | 464 | 349 |
| Piccotac 95 |  |  |  |  |  |
| Tufflo 6056 | 183 | 183 | 276 | 276 | 183 |
| Irg 1010 | 3 | 3 | 3 | 3 | 3 |
| HMV 177° C. | 15,900 | 1,828 | 30,000 | 11,800 | 4,900 |
| Adhesion initial |  |  |  |  |  |
| Peel cotton pli | 1.38 | 1.5 | 1.25 | 1.9 | 1.4 |
| Peel cotton g | 620 | 680 | 560 | 860 | 640 |
| Peel nylon pli | 1.25 | 2.3 | 1.3 | 2.1 | 1.8 |
| Peel nylon g | 560 | 1040 | 590 | 940 | 810 |
| Retention |  |  |  |  |  |
| Peel cotton pli |  | 1.8 |  |  | 1.9 |
| Peel cotton g |  | 810 |  |  | 860 |
| Peel nylon g |  | 2.4 |  |  | 2.2 |
| Peel nylon pli |  | 1,080 |  |  | 990 |

We claim:

1. A hot melt pressure sensitive positioning adhesive for use with an absorbent article comprising:
   (a) from 6 to less than 15 percent by weight of a blend of
      (i) from 40 to 95% by weight of the blend of a hydrogenated styrene-(butadiene or isoprene)-styrene block copolymer;
      (ii) from 5 to 60% by weight of the blend of a hydrogenated styrene-isoprene-styrene-isoprene block copolymer; and
      (iii) from 0 to 40% by weight of the blend of an amorphous ethylene/propylene copolymer having a weight average molecular weight of 9,000 to 30,000;
   (b) from 50 to 80 percent by weight of a tackifying resin which has an MMAP of at least 45° C.; and
   (c) from 5 to 35 percent by weight of a plasticizing oil.

2. The adhesive of claim 1 wherein the block copolymer of (ii) has a number average molecular weight of 65,000 to 130,000, a polystyrene content of 13 to 30% by weight, and a polystyrene block molecular weight of 6,000 to 15,000.

3. The adhesive of claim 1 wherein the block copolymer of (i) has a number average molecular weight of 65,000 to 300,000 and a polystyrene content of 10 to 40% by weight.

4. The hot melt adhesive of claim 1 wherein the viscosity of the adhesive is from 100 to 10,000 cPs at 177° C. and the adhesive exhibits no transfer after being peeled away from a fabric.

5. The adhesive of claim 3 wherein the viscosity of the adhesive is from 600 to 6,000 cPs at 177° C.

6. A hot melt pressure sensitive positioning adhesive for use with an absorbent article comprising:
   (a) from 6 to less than 15 percent by weight of a blend of
      (i) from 40 to 95% by weight of the blend of a hydrogenated styrene-(butadiene or isoprene)-styrene block copolymer;
      (ii) from 5 to 60% by weight of the blend of a hydrogenated styrene-isoprene-styrene-isoprene block copolymer; and
      (iii) from 5 to 40% by weight of the blend of an amorphous ethylene/propylene copolymer having a weight average molecular weight of 9,000 to 30,000;
   (b) from 50 to 80 percent by weight of a tackifying resin which has an MMAP of at least 45° C.; and
   (c) from 5 to 35 percent by weight of a plasticizing oil.

7. The adhesive of claim 6 wherein the block copolymer of (ii) has a number average molecular weight of 65,000 to 130,000, a polystyrene content of 13 to 30% by weight, and a polystyrene block molecular weight of 6,000 to 15,000.

8. The adhesive of claim 6 wherein the block copolymer of (i) has a number average molecular weight of 65,000 to 300,000 and a polystyrene content of 10 to 40% by weight.

9. The hot melt adhesive of claim 6 wherein the viscosity of the adhesive is from 100 to 10,000 cPs at 177° C. and the adhesive exhibits no transfer after being peeled away from a fabric.

10. The adhesive of claim 8 wherein the viscosity of the adhesive is from 600 to 6,000 cPs at 1770C.

\* \* \* \* \*